United States Patent [19]

Varterasian

[11] Patent Number: 4,480,473
[45] Date of Patent: Nov. 6, 1984

[54] ACOUSTIC INSPECTION METHOD

[75] Inventor: John H. Varterasian, Livonia, Mich.

[73] Assignee: General Motors Corporation, Detroit, Mich.

[21] Appl. No.: 498,633

[22] Filed: May 26, 1983

[51] Int. Cl.³ ............................................. G01N 29/00
[52] U.S. Cl. .................... 73/596; 73/40.5 A; 165/11 R
[58] Field of Search ............... 73/596, 599, 579, 582, 73/588, 592, 597, 40.5 A; 165/11 R

[56] References Cited

U.S. PATENT DOCUMENTS

| | | | |
|---|---|---|---|
| 3,753,260 | 8/1973 | Nelkin et al. | 73/40.5 A |
| 3,930,556 | 1/1976 | Kusuda et al. | 73/40.5 A |
| 4,289,019 | 9/1981 | Claytor | 73/40.5 A |
| 4,327,576 | 5/1982 | Dickey et al. | 73/40.5 A |
| 4,412,453 | 11/1983 | Nagai et al. | 73/599 |

Primary Examiner—Stephen A. Kreitman
Attorney, Agent, or Firm—R. L. Phillips

[57] ABSTRACT

There is disclosed an acoustic inspection method for determining whether the actual fluid flow path through a manufactured fluid flow system such as an evaporator core is of a prescribed length and thereby free of such manufacturing errors as cause a shortened or lengthened fluid flow path. The method comprises the steps of passing a test sound wave of predetermined frequency along the actual fluid flow path through the manufactured fluid flow system and comparing the phase angle of the test sound wave at the exit of the actual fluid flow path being inspected with that of a reference sound wave of the same frequency passing along the exactly prescribed fluid flow path length and on the basis that a difference in phase angle indicates that the fluid flow path being inspected is not of the prescribed length.

3 Claims, 7 Drawing Figures

ACOUSTIC INSPECTION METHOD

This invention relates to acoustic methods of inspection of fluid flow systems and more particularly to an acoustic inspection method for determining whether the actual fluid flow path through a manufactured fluid flow system is of a prescribed length.

In the manufacture of fluid flow systems such as heat exchanger cores, it is difficult, particularly on the assembly line, to detect internal leakage such as causes a reduced flow path length and resultantly reduced heat transfer capacity. For example, in the manufacture of air conditioner evaporator cores having an S-flow path, leakage at one of the returns as a result of improper assembly can cause a shunt resulting in a shortened refrigerant path and therefore reduced cooling capacity. Furthermore, once the evaporator core has been installed in the air conditioner system, detection is even more difficult and costly.

The method according to the present invention provides for acoustically inspecting such a manufactured fluid flow system for proper assembly rapidly and accurately on the production line at the completion of assembly. The present invention recognizes and utilizes the fact that such a manufactured fluid flow system when properly assembled free of manufacturing errors causing a shortened fluid flow path has a precise flow path length along which a sound wave can travel. Inspection is effected by passing a test sound wave of predetermined frequency along the actual fluid flow path through the manufactured fluid flow system. The phase angle of the test sound wave at the exit of the actual fluid flow path is then compared with that of a reference sound wave of the same frequency passing along the exactly prescribed fluid flow path length. Improper assembly is then detected on the occurrence of a certain difference in phase angle and thus does not require operator judgment so that with automation the method can be used in an unattended plant.

These and other objects, advantages and features of the present invention will become more apparent from the following description and drawing in which.

FIGS. 5(a), 5(b) and 5(c) are graphs showing the measured phase angles of three properly assembled and three improperly assembled evaporator cores at different excitation frequencies.

Figure 6:
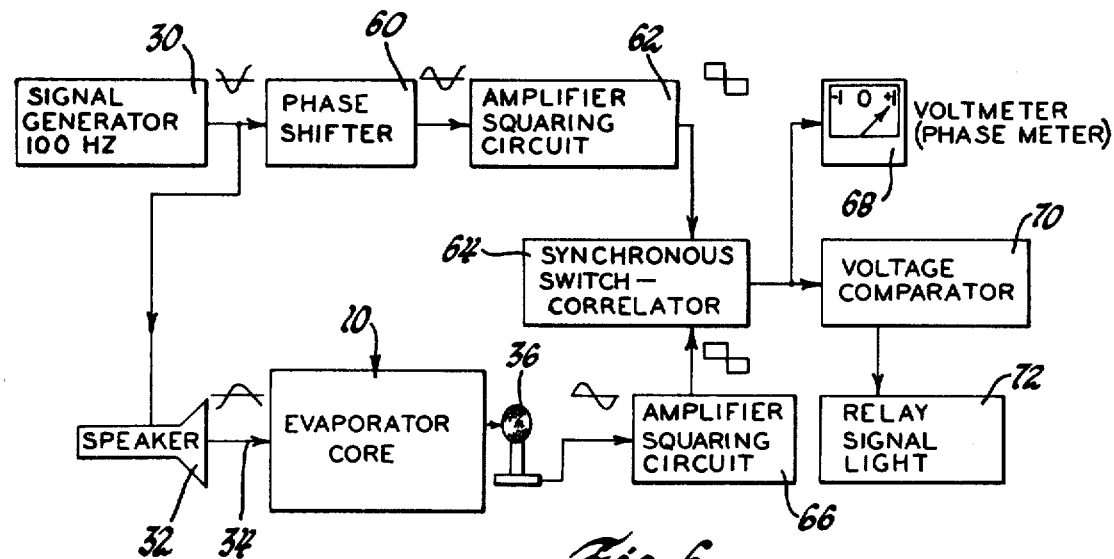

FIG. 6 is a diagrammatic view of a production form of apparatus for performing the acoustic inspection method of the present invention.

Figure 7:
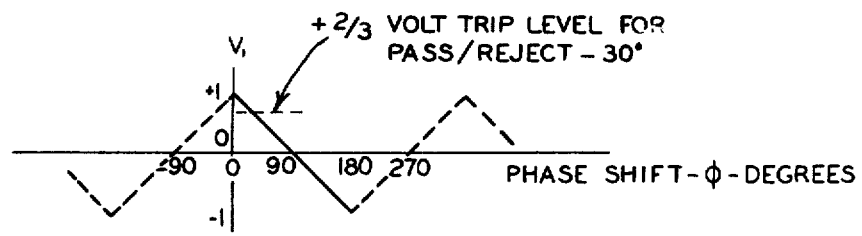

FIG. 7 is a graph showing the correlator phase shift versus DC volts for the apparatus in FIG. 6.

Figure 1:
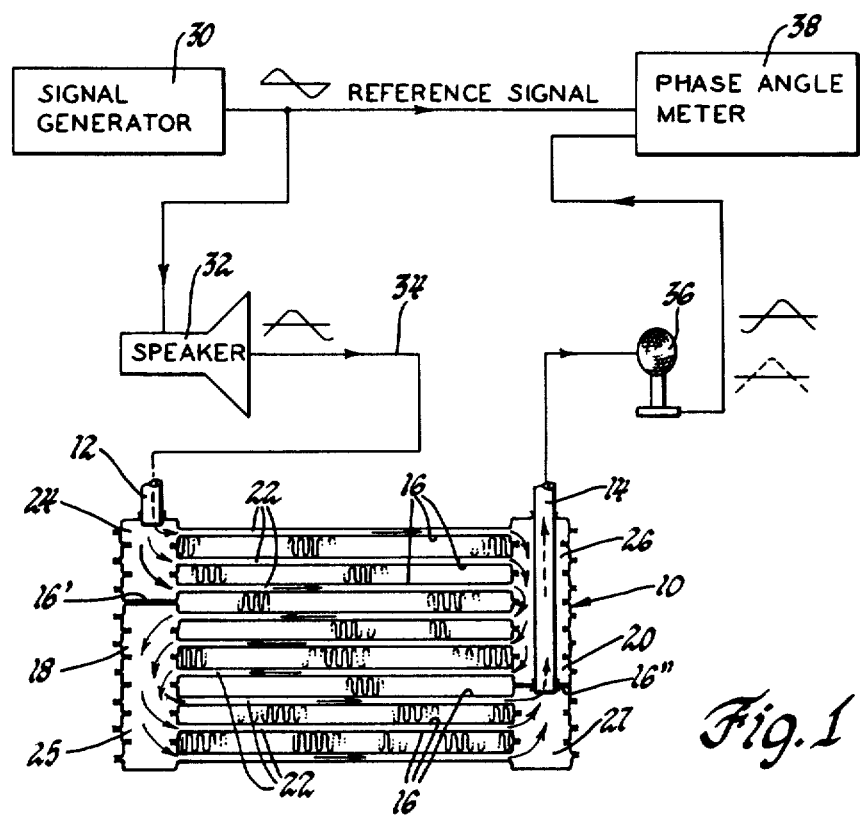
FIG. 1 is a cross-section of an air conditioner evaporator core with S-flow path that is properly constructed together with a diagrammatic view of apparatus for inspecting such core with the acoustic inspection method of the present invention.

Referring to FIG. 1, there is shown an air conditioner evaporator core 10 of the plate type having an S-flow path as shown by the arrows between an inlet pipe 12 and outlet pipe 14. The core is constructed of stacked tube plates 16 which are configured so as to cooperatively form two manifolds 18 and 20 interconnected by a plurality of tubes 22 which in this case total nine and are separated at the manifolds into three in each pass of the flow path across the core. The latter is accomplished by the inclusion of a blind tube plate 16' that divides the left hand manifold 18 into an upper inlet section 24 and a lower return section 25. The inlet section 24 connects with the inlet pipe 12 and the three upper pipes leading to the other manifold 20. The latter manifold is also divided but by a pierced tube plate 16" into an upper return section 26 and a lower outlet section 27. The upper return section 26 connects with the middle three as well as the upper three tubes 22 while the lower outlet section 27 connects with the lower three tubes 22 and with the outlet pipe 14 at the plate 16" which is pierced for this purpose and wherein the outlet pipe extends through the upper return section 26 for this connection. With such core construction, several possible assembly errors can result during the manufacture thereof. For example:

(1) The inlet pipe 12 and/or outlet pipe 14 may be short.
(2) The outlet pipe 14 may not be properly connected at the pierced tube plate 16".
(3) The blind tube plate 16' may be installed in the wrong location.
(4) A regular tube plate 16 may be installed instead of the blind tube plate 16'.
(5) A regular tube plate 16 may be installed instead of the pierced tube plate 16".

Figure 2:
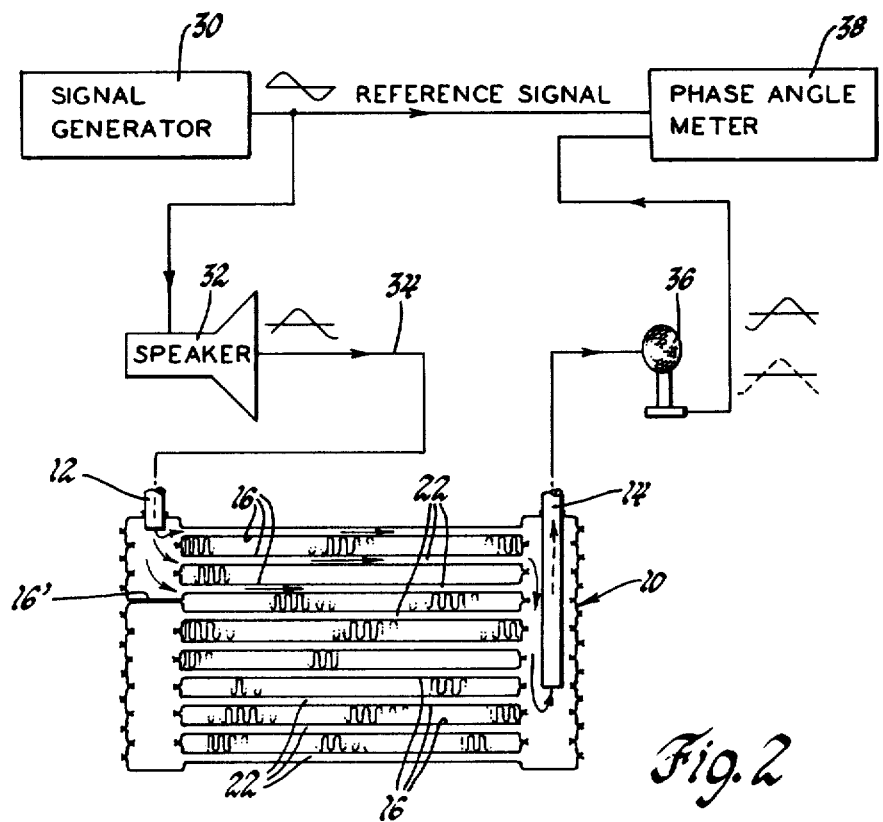
FIG. 2 is a view similar to FIG. 1 but with an improperly assembled evaporator core.

The result of a missing pierced tube plate 16" (error No. 5 above) is shown in FIG. 2 wherein the normal S-path has been short-circuited and the refrigerant (freon) flows only through the upper three tubes of the core and out the outlet pipe 14. With this type of improper assembly, the cooling resulting from the evaporator core may be reduced by as much as 66% of its normal value. Similarly, each of the other possible assembly errors can result in a different and shorter than normal refrigerant flow path and thereby reduced cooling capacity. None of these errors are readily detectable by conventional methods that are suitable for production line usage and detection after installation is even more difficult and costly.

The present invention performs the desired detection rapidly and accurately and with the use of apparatus rugged enough to withstand the production environment. The present invention utilizes the principle that a measure of the fluid flow system's flow path, in this case that of the evaporator core, is obtained by measuring the phase shift or change of a sound wave that is passed therealong. For example, a properly assembled core will have a standard phase change based on the transit time of the wave traveling a fixed distance, i.e. from the inlet pipe of the core to the outlet pipe. However, a core that has been improperly assembled with a resulting shorter flow path will have a correspondingly shorter transit time and phase change. As a result, the phase angle of the sound wave at the outlet pipe can be used to inspect for the proper length and to identify properly assembled cores from improperly assembled ones.

A basic form of apparatus for performing the method of the present invention is shown in FIGS. 1 and 2. The components are all conventional and comprise a sinusoidal signal generator 30 driving a loud speaker 32 with the resulting sound wave fed through a flexible tube 34 to the inlet pipe 12 of the evaporator core. A microphone 36 at the exit of the outlet pipe 14 generates a sine-wave voltage as the sound pressure wave impinges on it after having travelled through the core. The frequency of the microphone voltage is the same as that of the signal generator; however, the phase angle depends on the transit time through the core as well as on the speaker impedance, the length of the flexible tube 34 and the microphone characteristics all of which remain fixed. The phase angle of the sound wave through the core is measured with respect to that of a reference sine wave from the signal generator 30 by a phase angle meter 38. Whether or not the core has been properly assembled can be identified by the resulting phase angle difference as will now be demonstrated first with reference to the model in FIG. 3 and the relationship between flow path length and the resulting phase angle.

Figure 3:
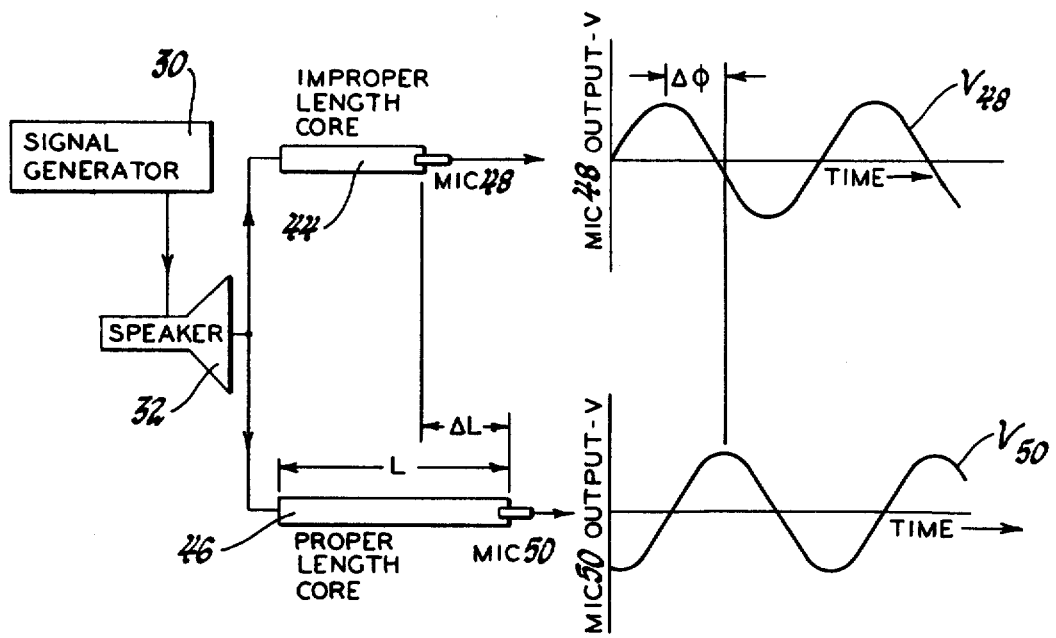
FIG. 3 is a diagrammatic view of a model together with graphs showing the phase angle shift principle of the acoustic inspection method of the present invention.

For illustrative purposes, the acoustic signal from the loud speaker 32 driven by the signal generator 30 in FIG. 3 is fed simultaneously to two tubes 44 and 46 of different lengths. The longer tube 46 with length L represents a properly assembled core, while the shorter one 44 with length $L-\Delta L$ represents an improperly assembled one. Microphones 48 and 50 at the closed end of the respective tubes were found to generate voltage wave forms in volts V with respect to time that are out of phase by a certain angle $\Delta\phi$ degrees as shown. This phase angle is directly related to $\Delta L$ and represents the phase lag of voltage $V_{48}$ with respect to voltage $V_{50}$. In the preferred practice however, it will be understood that the core phase angles are measured with respect to a reference voltage the signal generator (i.e. voltage) with a phase meter as in FIG. 1 and also as in FIG. 6 as later described.

The excitation frequency of the signal generator in FIGS. 1-3 is preferably such that the maximum phase angle change $\Delta\phi$ between properly assembled cores and improper ones is equal to or less than 180°. This may be expressed as follows:

$$\Delta\phi = 2\pi \frac{\Delta L}{\lambda} = \frac{2\pi \Delta L}{c/f} < \pi$$

where:
$\lambda$ = acoustic wavelength
c = speed of sound
f = excitation frequency This is because the phase meter as employed here has a unique and linear angle-voltage relationship only for angles between 0° and 180° (as well as for each successive ±180° band). For example, with a $\Delta L \approx 1.5$ m approximating an actual improper assembly as in FIG. 2 and with the speed of sound, C=345 m/sec, a viable excitation frequency of 115 Hz or less is calculated from the above equation in solving for f. That is:

$$f < \frac{c}{2\Delta L} = \frac{345 \text{ m/s}}{2 \times 1.5 \text{ m}}$$

$$f < 115 \text{ Hz}$$

However, higher excitation frequencies are possible but they limit the range of $\Delta L$ and require the system to operate in one of the other linear ranges of the phase meter like for instance 180°-360° or 360°-540°, etc. On the other hand, the phase meter could be used to provide unique angles between 0° and 360° but such an angle range would require an excitation frequency of up to 230 Hz and again limit the range of $\Delta L$. Unique phase measurements over a 360° range could also be made with an oscilloscope.

Figure 4:
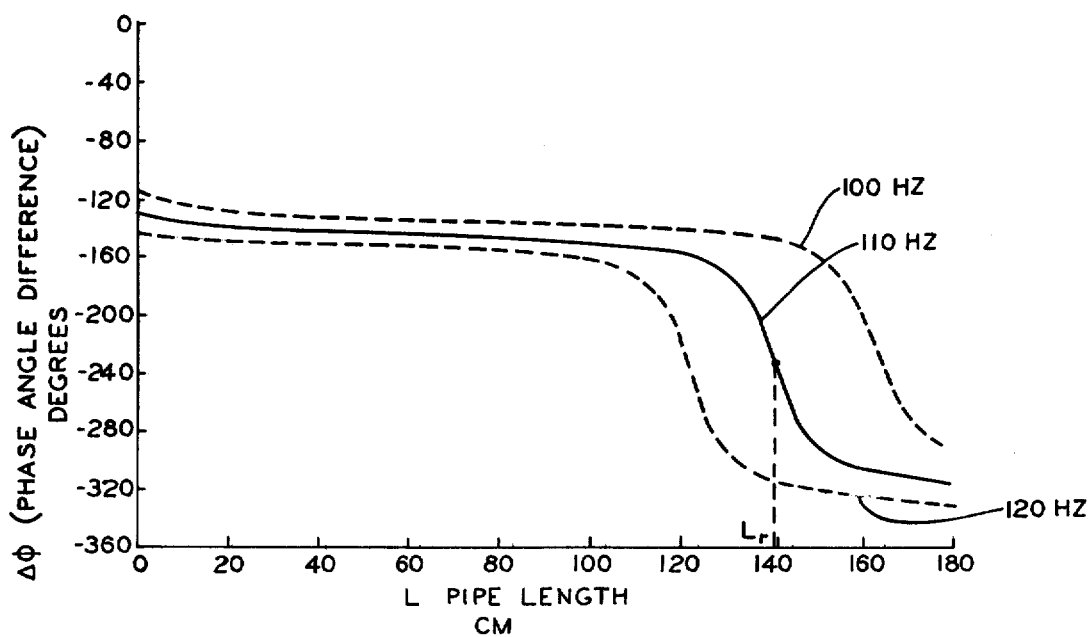
FIG. 4 is a graph showing the acoustic phase angle at the closed end of a pipe versus pipe length.

As shown by the solid-line curve in FIG. 4, the phase angle change $\Delta\phi$ does not vary linearly with the change in tube or pipe length $\Delta L$ and instead and because of an "organ pipe" type of resonance (one or more) remains relatively constant and then falls off at resonance to a lower plateau. This curve was obtained experimentally by measuring the phase angle change of a 110 Hz sound wave that was fed to a constant diameter pipe as the pipe length was changed from 0 to 200 cm (the latter being the approximate length of an actual construction of the evaporator core shown in FIG. 1). The phase angle change is the result of measuring the microphone signal phase angle with respect to the phase angle of the speaker excitation like in FIG. 3. As observed in FIG. 4, resonance occurs at the pipe length denoted $L_R$ where the curve has a maximum slope. Assuming that a sound wave through the evaporator core varies in a similar way and since the relationship is monotonic and each angle corresponds to a unique length, the phase angle can thus be used to inspect for the proper flow path length. Moreover, with the proper or optimum excitation frequency, the nonlinearity enhances the difference between a properly assembled core and an improper one at $L_R$ by increasing the angle change $\Delta\phi$ per unit change in length $\Delta L$.

The excitation frequency is preferably selected so that $L_R$ is between L and $L-\Delta L$ for the greatest angle difference to result between properly assembled cores and improper ones. As shown by the dashed-line curves of FIG. 4, the excitation frequency controls this point. For example, a frequency of 100 Hz increases $L_R$ whereas one of 120 Hz decreases this length. Where such curves are not available for the fluid flow system whose path length is to be inspected and where effective L's and $\Delta L$'s are not precisely known, the optimum excitation frequency is determined by an experimental procedure as will now be described.

Figure 5:
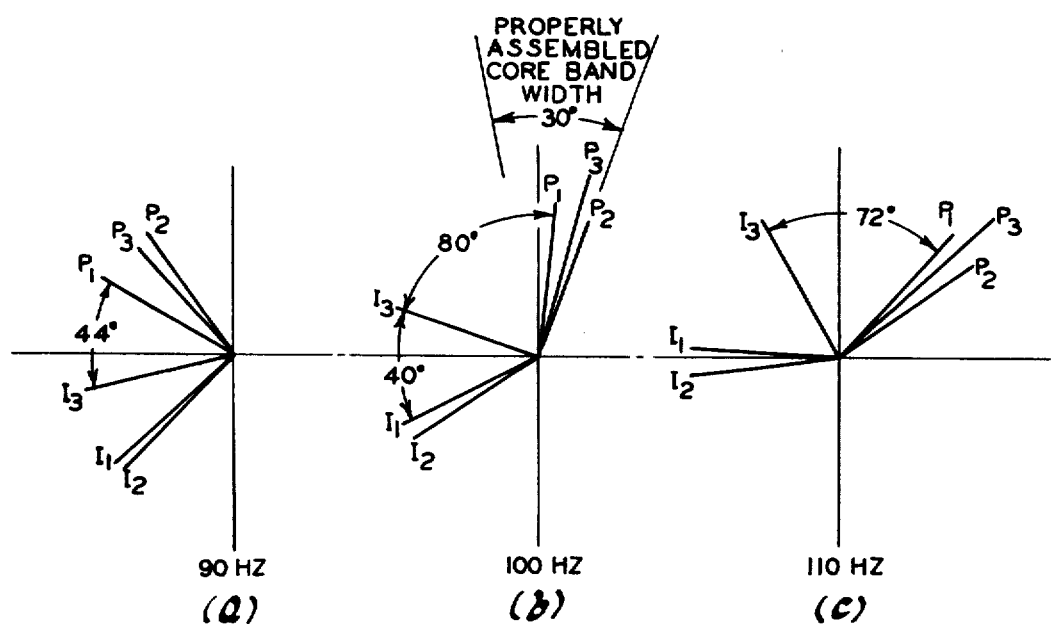

For example, to obtain the optimum excitation frequency for practicing the acoustic inspection method of the present invention as it relates to the evaporator core shown, phase angle measurements were made on three properly assembled cores and three improper ones; each of the latter with a different type of assembly error. FIG. 5 shows the resulting phase angle diagrams for the six cores measured with a conventional phase meter as in FIG. 1 using three different excitation frequencies: 90 Hz, 100 Hz, and 110 Hz. The phase diagrams of FIG. 5(b) clearly indicate that the optimum excitation is 100 Hz since this frequency resulted in the largest angular separation between the properly assembled cores designated as $P_1$, $P_2$, $P_3$ and the improperly assembled cores designated as $I_1$, $I_2$, $I_3$ (80° at 100 Hz vs. 44° at 90 Hz and 72° at 110 Hz). Clearly, a large separation makes the discrimination between properly assembled cores and improper ones more certain and reliable over long periods of time. In point of explanation, the small angular differences among the properly assembles cores $P_1$, $P_2$ and $P_3$ are probably due to length differences resulting from manufacturing tolerances whereas the angular differences observed between the improperly assembled cores $I_1$, $I_2$ and $I_3$ are due to the different types of defects resulting in substantially different flow paths through the respective cores. Furthermore, it will be appreciated that an evaporator with a different core configuration might require a different excitation frequency that can be determined by the method above.

The preferred form of the present invention as adapted for production usage is shown with the block diagram in FIG. 6. In addition to a phase angle readout which is intended only for the initial calibration, this apparatus is designed to give a "pass/reject" signal that can be used in a totally automated plant. As a result, operator judgment with regard to acceptable or faulty cores based on phase angle measurements is not required.

As in the FIG. 1 arrangement, a 100 Hz sine wave from the signal generator 30 is used to excite the loudspeaker 32 and to provide a reference for the acoustic phase angle measurement. In the production version, however, the reference signal is initially fed to an electro-mechanical phase shifter 60 of suitable conventional design implemented for example from an electro-mechanical resolver or a sine-cosine potentiometer and adapted to change the phase angle of this signal any desired amount from 0° through 360°. Typically, the phase would be shifted by simply rotating a shaft (not shown) a corresponding amount; i.e. the shaft angle corresponding to and determining the electrical phase angle of the output signal. The frequency and amplitude of the output signal are essentially unaltered from the input.

The electrical output from the phase shifter is fed to an amplifier and a squaring circuit 62 also of suitable conventional design. The result is a fixed amplitude square wave regardless of the amplitude of the input sine wave. The phase of the sine wave, however, is preserved in the square wave. The square wave is fed to one input terminal of a conventional synchronous switch 64 which may also be referred to as a correlator. This is because the output voltage vs $\Delta\phi$ is identical to the mathematical correlation function of two square waves.

As mentioned, the 100 Hz sine wave from the signal generator also excites the loudspeaker 32. And the acoustic signal from the loudspeaker is coupled to the inlet pipe of the evaporator core through the flexible plastic tube 34 as before.

The microphone 36 in the outlet pipe of the evaporator core produces a 100 Hz sine wave with a phase difference (from the signal generator voltage) that is attributable to the impedance of the speaker, the length of the tube connecting the speaker to the core, the microphone characteristics, and the flow path within the core. Since the speaker, connecting tube, and microphone remain fixed when inspecting different cores, a phase angle change indicates a change in the core fluid flow path only.

The microphone signal is fed to a conventional amplifier and squaring circuit 66 like the generated signal from the phase shifter 60. Again, regardless of the amplitude of the microphone voltage, the resulting square wave is fixed in amplitude and has the phase angle of the sine wave. The test channel square wave is fed to the second input terminal of the correlator 64.

With two square waves fed to the input terminals, the output of the correlator 64 is a DC voltage that varies linearly with the phase difference $\Delta\phi$ between the square waves as shown in FIG. 7. For instance, when the square waves are in phase, $\Delta\phi = 0°$ (100% correlation) and the correlator output is a maximum, e.g. +1 volt. As the phase difference between the square waves increases, the output voltage decreases along the solid straight line as shown. At $\Delta\phi = 90°$ (no correlation), the correlator output is 0 volts. As the phase angle difference approaches 180° the voltage becomes $-1$ denoting a negative correlation. As a result, a unique relationship between phase angle difference and voltage results between $\Delta\phi = 0°$ and $\Delta\phi = 180°$, the region where the function is monotonically decreasing. For phase angles less than 0° and greater than 180°, the output of the correlator 64 follows the dashed lines in FIG. 7 and repeats the voltages in the 0°-180° zone. To maintain uniqueness, the system in general is used only to measure phase angles in the initial 0°-180° range. However, any of the linear 180° bands of FIG. 7 could be used if the application warranted such. For instance, if the expected change $\Delta L$, in a fluid flow path was very small, a higher excitation frequency could be used that can be calculated by the method in FIG. 3. Such an excitation would cause the system to operate several 180° bands from the origin of FIG. 7 but still within one particular (linear) 180° band. In such a mode, the small $\Delta L$ would be measured by a complete 180° phase change, thus increasing the sensitivity of the inspection process.

The correlator voltage is fed to a conventional zero centered voltmeter 68 with a range of for instance $\pm 1$ volt. The meter 68 in effect becomes a phase meter with the extreme right end of the meter (+1 volt) corresponding to a phase angle of 0°, the center of the meter being 90° and the far left end ($-1$ volt) being 180°.

The apparatus in FIG. 6 is calibrated as follows. A properly assembled evaporator core is placed as reference in the loop. The phase shifter 60 is then adjusted until the phase meter 68 indicates 0° (+1 volt). As a result, it follows that the reference square wave is in phase with the test square wave resulting from the properly assembled core. The phase shifter need not be changed again. Thereafter, when a test core is placed in the loop and the phase meter indicates 0°, or near 0°, the core is indicated as properly assembled. On the other hand, if the phase meter indicates a substantially different phase angle, the core is indicated as improperly assembled. For instance, if the FIG. 6 apparatus was calibrated with the properly assembled core $P_1$ of FIG. 5(b), then when the improperly assembled core $I_3$ of this figure was being inspected, the phase meter 68 would indicate $\Delta\phi = 80°$. This would be the smallest angle to identify an improperly assembled core assuming that the only types of defects were those shown by $I_1$, $I_2$ and $I_3$ of FIG. 5(b). Other cores like $I_1$ would result in a phase meter indication of $\Delta\phi = 120°$; i.e. more needle deflection.

The above calibration procedure applies to fluid assemblies like the evaporator core where the various possibilities of improper assembly only shorten the fluid flow path. In assemblies where both longer and shorter flow paths can result, the calibration would be as follows. The reference square wave is adjusted to be 90° out-of-phase with the signal square wave resulting from a proper assembly. In such a configuration, all improper assemblies (too long or short a flow path) would yield square waves that are 90° from the reference. As a result, the zone near the center of the phase meter (90° or 0 volt) would indicate only proper assemblies. The zone at the right end of the meter (0° or +1 volt) would indicate an improper assembly with a longer than normal fluid flow path while the zone at the left end (180° or $-1$ volt) would indicate one with a shorter than normal path. On the other hand, if an improper assembly would have only a longer fluid flow path, the reference square wave is adjusted to be 180° from the square wave resulting from a proper assembly. Thereafter, proper assemblies would be indicated by the zone at the left end of the phase meter 68 and improper ones would be indicated by phase angles near the center or towards the right end.

In addition, automatic pass/reject detection is simply made available by feeding the correlator output voltage to a conventional voltage comparator 70 as shown in FIG. 6. The comparator 70 produces an output voltage that energizes a relay 72 only when the input has exceeded a pre-set level ... near +1 volt or $\Delta\phi = 0°$, i.e. one that defines a properly assembled core. The relay may be used in a signal light as shown such that it energizes a green light to indicate a properly assembled core to the operator or the relay closure can be used to invoke a pass signal in an automated assembly line (not shown). Conversely, if the voltage to the comparator is too low to trip the relay (indicating an improperly assembled core with a phase angle substantially different from 0°), an improperly assembled core would be indicated by a red light or a rejection could be invoked in the automated line.

With the phase angle diagrams of FIG. 5(b), the properly assembled cores can be defined as those in a phase angle bandwidth between 0° and 30° as indicated while improperly assembled ones would be those with phase angles greater than 30°. With the voltage vs. phase angle characteristics of the correlator in FIG. 7 the desired separation occurs with the voltage comparator adjusted to trip at $+\frac{2}{3}$ V (30° phase angle). As a result, once the system is set, no operator judgment is required in identifying the properly and improperly assembled cores. But it will be understood that the trip level can be changed if new data indicates a pass bandwidth different than 30°.

The above described embodiment is illustrative of the present invention which may be modified within the scope of the appended claims.

The embodiments of the invention in which an exclusive property or privilege is claimed are defined as follows:

1. An acoustic inspection method for determining whether the actual fluid flow path through a manufactured fluid flow system such as a heat transfer core is of a prescribed length and thereby free of such manufacturing errors as cause a shortened or lengthened fluid flow path comprising the steps of:
   (1) passing a test sound wave of predetermined frequency along the actual fluid flow path through the manufactured fluid flow system,
   (2) comparing the phase angle of the test sound wave at the exit of the actual fluid flow path being inspected with that of a reference sound wave of the same frequency passing along the exactly prescribed fluid flow path length, and
   (3) detecting whether or not the actual fluid flow path being inspected is of the prescribed length on the basis that the occurrence of a prescribed difference in phase angle indicates that the fluid flow path being inspected is not of the prescribed length.

2. An acoustic inspection method for determining whether the actual fluid flow path through a manufactured fluid flow system such as a heat transfer core is of prescribed length and thereby free of such manufacture errors as cause a shortened or lengthened fluid flow path comprising the steps of:
   (1) generating both an electrical test signal and reference signal of sinusoidal wave form and the same frequency,
   (2) transforming the electrical test signal into an acoustic test sound wave of the same frequency,
   (3) passing the acoustic test sound wave along the actual fluid flow path through the manufactured fluid flow system,
   (4) converting the electrical reference signal to a square wave form of fixed amplitude while retaining the phase of the sine wave,
   (5) converting the acoustic test sound wave at the exit of the actual fluid flow path to an electrical test signal of square wave form of fixed amplitude while retaining the phase of the sine wave,
   (6) shifting the square wave electrical reference signal so as to be in phase with the square wave electrical test signal when the actual fluid flow path is of the prescribed length,
   (7) correlating the shifted square wave electrical reference signal and the square wave electrical test signal so as to produce a test output signal that varies with the phase angle difference between these signals, and
   (8) detecting whether or not the actual fluid flow path being inspected is of the prescribed length according to a prescribed test output signal.

3. An acoustic inspection method for determining whether the actual fluid flow path through a manufactured fluid flow system such as a heat transfer core is of prescribed length and thereby free of such manufacture errors as cause a shortened or lengthened fluid flow path comprising the steps of:
   (1) generating both an electrical test signal and reference signal of sinusoidal wave form and the same frequency,
   (2) transforming the electrical test signal into an acoustic test sound wave of the same frequency,
   (3) passing the acoustic test sound wave along the actual fluid flow path through the manufactured fluid flow system,
   (4) converting the electrical reference signal to a square wave form of fixed amplitude while retaining the phase of the sine wave,
   (5) converting the acoustic test sound wave at the exit of the actual fluid flor path to an electrical test signal of square wave form of fixed amplitude while retaining the phase of the sine wave,
   (6) shifting the square wave electrical reference signal so as to be in phase with the square wave electrical test signal when the actual fluid flow path is of the prescribed length,
   (7) correlating the shifted square wave electrical reference signal and the square wave electrical test signal so as to produce a test output signal that varies linearly with the phase angle difference between these signals,
   (8) setting the frequency of the test and reference signals so as to obtain the largest phase angle difference therebetween at a fluid flow path length intermediate the prescribed length and the actual length that can result from manufacturing error, and
   (9) detecting whether or not the actual fluid flow path being inspected is of the prescribed length according to a prescribed test output signal.

* * * * *

UNITED STATES PATENT AND TRADEMARK OFFICE
CERTIFICATE OF CORRECTION

PATENT NO. : 4,480,473
DATED : November 6, 1984
INVENTOR(S) : John I. Varterasian It is certified that error appears in the above—identified patent and that said Letters Patent is hereby corrected as shown below:

Column 3, line 31, after "voltage", (first occurrence) delete "the signal generator", and after "i.e.", insert -- the signal generator --.

Signed and Sealed this

Ninth Day of April 1985

[SEAL]

Attest:

DONALD J. QUIGG

Attesting Officer

Acting Commissioner of Patents and Trademarks